United States Patent [19]

Wehle et al.

[11] Patent Number: 5,600,020
[45] Date of Patent: Feb. 4, 1997

[54] PROCESS FOR THE PREPARATION OF ALKOXYLATES USING ESTER COMPOUNDS AS CATALYST

[75] Inventors: Detlef Wehle, Niedernhausen; Gernot Kremer, Kelkheim; Ignaz Wimmer, Winhöring, all of Germany

[73] Assignee: Hoechst Aktiengesellschaft, Germany

[21] Appl. No.: 350,413

[22] Filed: Dec. 6, 1994

[30] Foreign Application Priority Data

Dec. 7, 1993 [DE] Germany .................. 43 41 576.8

[51] Int. Cl.⁶ .................. C07C 43/11; C07C 41/01
[52] U.S. Cl. .................. 568/618; 568/678; 568/679; 568/680
[58] Field of Search .................. 568/678, 679, 568/680, 618

[56] References Cited

U.S. PATENT DOCUMENTS 4,894,485  1/1990  Behler et al. ..................... 568/618
4,996,364  2/1991  Behler et al. ..................... 568/618

FOREIGN PATENT DOCUMENTS 2094556  10/1993  Canada .
0295578  12/1988  European Pat. Off. .
0337239  10/1989  European Pat. Off. .
0566956  10/1993  European Pat. Off. .
0796508   6/1958  United Kingdom .

*Primary Examiner*—Gary Geist
*Assistant Examiner*—Dwayne C. Jones
*Attorney, Agent, or Firm*—Connolly & Hutz

[57] ABSTRACT

According to the invention, the alkoxylation of compounds containing active hydrogen atoms is carried out in the presence of specific alkaline earth metal salts of alkyl or alkenylsuccinic monoesters as catalyst. The alkoxylates obtained have a narrow homolog distribution and a good appearance.

13 Claims, No Drawings

PROCESS FOR THE PREPARATION OF ALKOXYLATES USING ESTER COMPOUNDS AS CATALYST

BACKGROUND OF THE INVENTION

1. Field of the Invention

This invention relates to the alkoxylation of an active hydrogen-containing compound with an alkylene oxide in the presence of a catalyst.

2. Description of the Prior Art

Alkoxylates are of great importance, for example as intermediates in derivatization processes and as nonionic components in industrial and cosmetic detergents, cleaners and cleansing compositions. They are also employed in a large number of applications as emulsifiers, dispersants and the like. In these applications the desire is frequently for those alkoxylates which exhibit a narrow distribution of the alkoxylation homologs. This distribution is determined essentially by the catalyst used in the alkoxylation reaction.

It was disclosed a long time ago, for example by British Patent 796 508, that antimony pentahalide catalysts lead, in the reaction of compounds containing active hydrogen atoms (for example in the form of hydroxyl groups) with alkylene oxide (for example ethylene oxide and/or propylene oxide), to alkoxylates having a narrow homolog distribution (narrow-range alkoxylates). This advantage is countered by the disadvantage of the difficulty of handling the antimony pentahalides (severe fuming, corrosive, sensitive to hydrolysis) and the unsatisfactory color quality of the alkoxylate.

U.S. Pat. No. 4 996 364 describes unsubstituted polycarboxylic monoesters in the form of alkaline earth metal salts as catalyst for the alkoxylation of compounds containing active hydrogen atoms, such as fatty alcohols. Among the polycarboxylic acids mentioned is succinic acid, although likewise unsubstituted. Although these alkaline earth metal salts of polycarboxylic monoesters possess advantages in comparison to antimony pentahalides as catalyst, they still always leave something to be desired in respect of the homolog distribution and/or appearance of the resulting alkoxylates.

Canadian Patent Application 2 094 556 describes alkali metal or alkaline earth metal salts of alkyl- or alkenylsuccinic monoesters as anticorrosion agents for metalworking, the alkyl or alkenyl substituent containing from 8 to 30 carbon atoms, preferably from 9 to 15 carbon atoms. The document gives no mention or indication in the direction of any other possible application for these half-esters of the substituted succinic acid. It has now been surprisingly found that, when alkaline earth metal salts of alkyl- or alkenylsuccinic half-esters are used as catalyst for alkoxylations, a further improvement is achieved with regard to the narrow homolog distribution and appearance of the resulting alkoxylates.

SUMMARY OF THE INVENTION

The process according to the invention for the preparation of alkoxylates by alkoxylating compounds containing at least one active hydrogen atom in the presence of a salt of a succinic monoester as catalyst comprises carrying out the alkoxylation in the presence of at least one alkaline earth metal salt of an alkyl- or alkenylsuccinic monoester, of the formulae (I) and (II) below

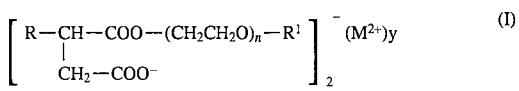

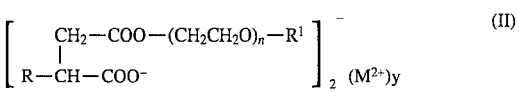

in which

R is $C_8$ to $C_{30}$ alkyl or $C_8$ to $C_{30}$ alkenyl, n is a number from 0 to 6, $R^1$ is $C_1$ to $C_{18}$ alkyl or $C_3$ to $C_{18}$ alkenyl or hydrogen, if n is 1 or >1, M is Ba, Ca or Sr, and Y is a number from 0.9 to 1.8.

In the formulae (I) and (II) R is preferably a $C_9$ to $C_{20}$ alkyl or a $C_9$ to $C_{20}$ alkenyl, n is preferably a number from 0 to 3, $R^1$ is preferably a $C_1$ to $C_{12}$ alkyl or a $C_3$ to $C_{12}$ alkenyl, and may preferably also be a hydrogen atom if n is 1 or >1, and y is preferably a number from 1 to 1.3 and particularly preferably 1. For reasons of convenience M is preferably Ca. The alkenyl groups preferably have from 1 to 3 double bonds. The alkyl and alkenyl groups may be linear or branched. Alkyl and alkenyl may also be present in the form of mixtures, for example in the form of a mixture of $C_{12}$ and $C_{14}$ alkyl ($C_{12/14}$ alkyl) or $C_{12}$ and $C_{14}$ alkenyl ($C_{12/14}$ alkenyl) or of $C_{12}$ and of $C_{14}$ alkyl and alkenyl groups. Among the alkaline earth metal salts, to be used according to the invention, of a succinic half-ester substituted with an alkyl group or an alkenyl group, those substituted with an alkenyl group are preferred; i.e. R in formulae (I) and (II) is preferably one of the alkenyl groups mentioned. The radical $R^1$ resulting from the esterification alcohol, on the other hand, is preferably one of the alkyl groups mentioned. Examples of alkyl and alkenyl radicals, therefore, are methyl, propyl, butyl, isobutyl, octyl, octenyl, decyl, decenyl, dodecyl (lauryl), dodecenyl, oleyl, octadecadienyl, octadecatrienyl and tallow-fatty alkyl.

It has been found that an even higher effectiveness with regard to catalytic activity and narrow homolog distribution is achieved by carrying out alkoxylation in the presence of at least one succinic monoester salt of the formulae (I) and (II) if from 10 to 70%, preferably from 30 to 60%, of the titratable alkalinity of said salts have been neutralized using an inorganic acid which forms salts of low solubility in water with the cations Ba, Ca and Sr. Preferred mineral acids are sulfuric acid ($H_2SO_4$) and sulfurous acid ($H_2SO_3$), and also phosphoric acid ($H_3PO_4$) and phosphorous acid ($H_3PO_3$).

DETAILED DESCRIPTION

The alkaline earth metal salts of alkyl- and/or alkenyl-succinic half-esters to be used in accordance with the invention (i.e. positional isomers which are generally present as a mixture) are known and commercially available, for example as ®Hostacor (®=registered trademark of Hoechst). They are preferably prepared by reacting (esterifying) corresponding alkyl- or alkenylsuccinic anhydrides, or alternatively the corresponding acid compounds, with alcohols of the formula $R^1$—OH or alkoxylated alcohols of the formula $R^1$—$(OCH_2CH_2)_n$—OH, where $R^1$ and n are as defined, in equimolar quantities, and preparing the corresponding alkaline earth metal salts from the resulting alkyl- or alkenylsuccinic half-esters using basic alkaline earth metal compounds, for example the acetates, oxides, carbonates or hydroxides. The esterification is preferably carried out at a temperature of from 60° to 150° C. without using a solvent, under a nitrogen atmosphere. The half-ester is then reacted with preferably one oxide, carbonate or hydroxide compound of barium, calcium or strontium, the hydroxides being preferred, to convert it into the salt of these alkaline earth metals. The alkaline earth metal compound is employed, corresponding to the value y in the formulae (I) and (II), in a quantity of from 0.9 to 1.8 mol, preferably from 1 to 1.3 mol and particularly preferably in a quantity of 1 mol per 2 mol of half-ester compound. The reaction of half-ester and alkaline earth metal compound is preferably carried out at a temperature of from 60° to 160° C. using a low-boiling, inert, organic solvent, such as toluene and xylene, and/or a higher-boiling, inert, organic solvent, such as hydrocarbons, acetals and ethers having a boiling point >150° C. at atmospheric pressure. The water of reaction formed is removed. The reaction time is about 2 hours. When salt formation has ended the low-boiling solvent is removed, for example on a rotary evaporator. In this way, in general, an approximately 60% strength by weight solution of the succinic half-ester salts to be employed in accordance with the invention is obtained in the form of an oil. This presupposes that the solvent which has been employed is a mixture of low- and higher-boiling solvents.

The abovementioned partial neutralization of the titratable alkalinity of the alkaline earth metal salts of the alkyl- or alkenylsuccinic half-ester is preferably carried out by adding the mineral acid in the form of a from 10 to 50% strength by weight aqueous solution to the succinic half-ester (at from about 20° to 100° C.) in the stoichiometric quantity required for the degree of partial neutralization (of the titratable alkalinity determined beforehand) which is sought, after which the water present in the reaction product is removed by heating at from about 50° to 150° C., if desired with the application of vacuum. The product obtained is of liquid to semisolid consistency.

The quantity of catalyst according to the invention can vary within broad limits and is in general from 0.1 to 5% by weight, preferably from 0.5 to 3% by weight, these percentages by weight being based on the weight of the product to be alkoxylated. The catalyst is added to the product to be alkoxylated in the quantity indicated. It can also be generated in situ, for example by first adding to the fatty alcohol to be alkoxylated a defined quantity of an oxide, carbonate or hydroxide of barium, calcium or strontium, the hydroxides being preferred, adding the corresponding stoichiometric quantity of substituted succinic anhydride compound, said quantity resulting from formulae (I) and (II), and then drying the mixture, applying a vacuum if desired, before beginning the alkoxylation. The in situ variant may also comprise the partial neutralization described.

The alkoxylation of the compounds containing active hydrogen atoms using the products according to the invention as catalyst is carried out conventionally, i.e. at a temperature of from 60° to 200° C., preferably from 100 to 180° C., and at a pressure of from about 0.5 to 6 bar, the alkylene oxide being metered in in portions or continuously. The quantity of alkylene oxide is in general from 1 to 30 mol, preferably from 2 to 20 mol and in particular from 2 to 15 mol, per mole of compound to be alkoxylated. The resulting alkoxylate can generally be employed without separating off the catalyst beforehand.

The alkoxylation catalyst according to the invention has a high catalytic activity and leads, in a relatively short reaction time, to practically complete conversion and a high yield. The alkoxylate has a narrow homolog distribution and is also colorless and in many cases clear, and therefore has a good appearance. A further advantage is that the catalyst proposed in accordance with the invention can also be formed easily in situ.

Although the nature of the alkylene oxides and of the compounds containing active hydrogen atoms is not critical for the process according to the invention, the following comments are made with respect to it:

The alkylene oxides employed are preferably ethylene oxide, propylene oxide and/or butylene oxide, with preference being given to ethylene oxide and/or propylene oxide. Ethylene oxide is particularly preferred.

Examples of compounds containing active hydrogen atoms are those containing hydroxyl groups, and also amine compounds and acid compounds such as fatty acids, those mentioned initially being preferred. Examples of compounds containing hydroxyl groups are alcohols, amino alcohols, perfluoroalkyl alcohols, glycols, glycol monoethers, glycerol, phenols, cresols and the like, with alcohols being preferred. They may be derived from natural sources or from synthetic processes, may be primary, linear or branched, saturated or unsaturated and mono- or polyhydric, examples being oxo alcohols, Guerbet alcohols, Ziegler alcohols, fatty alcohols and the like. Preferred alcohols are the primary, straight-chain or branched $C_3$ to $C_{24}$ alkanols, preferably $C_6$ to $C_{18}$ alkanols (fatty alcohols) or mixtures thereof, for example mixtures of $C_{12}$ and $C_{14}$ alkanol ($C_{12/14}$). Examples of the preferred alcohols are butanol, amyl alcohol, hexanol, nonanol, isononyl alcohol, decanol, undecanol, isoundecanol, lauryl alcohol, isotridecyl alcohol, stearyl alcohol, coconut fatty alcohol and mixtures thereof, and also 2-ethylhexanol, 2-hexyldecanol, 2-octyldecanol and similar Guerbet alcohols.

The invention is now illustrated in more detail with reference to examples and comparative examples.

The homolog distribution of the alkoxylates obtained in the examples and comparative examples was determined by capillary gas chromatography after preceding derivatization. The parameter given for the homolog distribution is the so-called Q value in accordance with the equation $Q=n^* \cdot p^2$, in which $n^*$ is the average adduct number (average degree of alkoxylation) and p is the percent by weight of the most frequently occurring alkoxylation homolog. As is known, this Q value is a good measurement parameter especially when the alkoxylates concerned are those having an essentially equal average degree of alkoxylation. Higher values of Q indicate a more selective alkoxylation and an alkoxylate having a narrower homolog distribution.

Preparation of the catalysts according to the invention:

EXAMPLES 1A to 10A 1 mol of alkenylsuccinic anhydride is reacted with 1 mol of alcohol, 1 mol of ethylene glycol (Example 4A) or 1 mol of triethylene glycol monomethyl ether (Example 3A) at from 60° to 150° C. under an $N_2$ atmosphere to give the corresponding alkenylsuccinic half-ester. Depending on the alcohol, the reaction time is between 3 and 25 hours at an overpressure of from 0 to 2 bar. 1 mol of the alkenylsuccinic half-ester prepared in this way, 600 ml of toluene, 228 g of mineral oil and 0.55 mol of alkaline earth metal hydroxide are stirred together at room temperature, and the water which forms is removed azeotropically over about 2 hours at from 100° to 120° C. 10 g of filter aid are then added, the mixture is filtered, and the toluene employed is removed from the clear filtrate on a rotary evaporator. About 60% strength by weight solutions of the alkenylsuccinic half-ester alkaline earth metal salts are obtained as clear, reddish brown oils.

EXAMPLES 11B to 13B (partial neutralization)

0.4 times the stoichiometric quantity of $H_2SO_4$ (as a 25% strength by weight aqueous solution) necessary to neutralize the alkalinity is added to 100 g of an alkenylsuccinic half-ester calcium salt having a titratable alkalinity of alkali number 106 (mg of KOH/g), the mixture is stirred, and water is removed under vacuum (20 mbar) at 90° C. A yellow, pasty substance is obtained.

Examples 1A to 10A and 11B to 13B are summarized in Table 1 below with reference to formulae (I) and (II):

TABLE 1

| Example | R | $R^1$ | n | M | y |
|---|---|---|---|---|---|
| 1A | iso-$C_{12}$-alkenyl | isobutyl | 0 | Ca | 1 |
| 2A | iso-$C_{12}$-alkenyl | octyl | 0 | Ca | 1 |
| 3A | iso-$C_{12}$-alkenyl | methyl | 3 | Ca | 1 |
| 4A | iso-$C_{12}$-alkenyl | H | 1 | Ca | 1 |
| 5A | iso-$C_{12}$-alkenyl | lauryl | 0 | Ca | 1 |
| 6A | iso-$C_9$-alkenyl | isobutyl | 0 | Ca | 1 |
| 7A | n-$C_{12/14}$-alkenyl | methyl | 0 | Ca | 1 |
| 8A | n-$C_{18}$-alkenyl | isobutyl | 0 | Ca | 1 |
| 9A | iso-$C_{12}$-alkenyl | isobutyl | 0 | Ba | 1 |
| 10A | iso-$C_{12}$-alkenyl | isobutyl | 0 | Sr | 1 |
| 11B | iso-$C_{12}$-alkenyl | isobutyl | 0 | Ca + $H_2SO_4$ | 1 |
| 12B | iso-$C_{12}$-alkenyl | isobutyl | 0 | Ca + $H_3PO_4$ | 1.8 |
| 13B | iso-$C_{12}$-alkenyl | $C_{12/14}$-alkyl | 0 | Ca + $H_2SO_4$ | 1 |

Alkoxylation in the presence of the catalysts of Examples 1A to 10A and 11B to 13B:

EXAMPLES 1 to 15

1 mol of a fatty alcohol (that is, for example, 194 g of $C_{12/14}$ alkanol) are weighed into a glass pressure reactor and, by heating and applying a vacuum or alternatively by passing in nitrogen, the alcohol is dried until its water content does not exceed 0.10% by weight. Then 0.9% by weight, based on fatty alcohol, of catalyst (for example 2.9 g of the 60% strength by weight solution of catalyst 1A) is added. After heating the mixture to 160° C., the metered addition of ethylene oxide (EO) is begun, and all of the envisaged quantity of EO is injected at from 150° to 180° C. at the rate at which it is consumed by reaction (which can be determined from the pressure decrease in the reactor).

The results obtained with the catalysts according to the invention using this alkoxylation procedure are summarized in Table 2 below, which also contains Example 16.

EXAMPLE 16

(in situ formation of the catalyst)

194 g of $C_{12/14}$ alkanol (1 mol) are weighed into a glass pressure reactor, and 1.95 g of iso-$C_{12}$-alkenylsuccinic anhydride (7.34 mmol) are added. After the mixture has been stirred for a short time, 0.28 g of 97% by weight $Ca(OH)_2$ (3.67 mmol) is metered in, and the mixture is stirred at 130° C. for 1 hour. Then 1.96 g of 11% strength by weight $H_2SO_4$ (2.20 mmol) are added at 90° C., corresponding to about 60% neutralization of the basicity of the alkaline earth metal compound. Stirring is then carried out at reduced pressure (residual pressure about 20 mbar) for about 2 hours at 130° C. in order to remove the water. The reaction with the epoxide is then carried out at a temperature of from 150° to 170° C.

TABLE 2

| Example | Catalyst | Catalyst quantity (% by wt.) | Initial alcohol | mol of EO/ mol of alcohol | Q index |
|---|---|---|---|---|---|
| 1 | 1A | 0.9 | n-$C_{12/14}$ | 4 | 1100 |
| 2 | 2A | 0.9 | n-$C_{12/14}$ | 4 | 1000 |
| 3 | 3A | 0.9 | n-$C_{12/14}$ | 4 | 1020 |
| 4 | 4A | 0.9 | n-$C_{12/14}$ | 4 | 1050 |
| 5 | 5A | 0.9 | n-$C_{12/14}$ | 4 | 1000 |
| 6 | 6A | 0.9 | n-$C_{12/14}$ | 4 | 1000 |
| 7 | 7A | 0.9 | n-$C_{12/14}$ | 4 | 1030 |
| 8 | 8A | 0.9 | n-$C_{12/14}$ | 4 | 1030 |
| 9 | 9A | 0.9 | n-$C_{12/14}$ | 4 | 1000 |
| 10 | 10A | 0.9 | n-$C_{12/14}$ | 4 | 1000 |
| 11 | 12B | 0.9 | n-$C_{12/14}$ | 4 | 1850 |
| 12 | 1A | 0.9 | n-$C_{16/18}$ | 8 | 1350 |
| 13 | 11B | 0.9 | n-$C_{12/14}$ | 4 | 1840 |
| 14 | 11B | 0.9 | n-$C_{12/14}$ | 6 | 2400 |
| 15 | 11B | 0.9 | n-$C_{12/14}$ | 11 | 3500 |
| 16 | in situ formation | 1.0 | n-$C_{12/14}$ | 4 | 1770 |

The alkoxylates of Examples 1 to 10 and 12 are clear and those of Examples 11 and 13 to 16 are slightly cloudy.

Comparative Examples 1 and 2

The ethoxylation reactions of Examples 1 and 14 were repeated (i.e. ethoxylation with 4 and 6 mol, respectively, of EO per mole of initial alcohol), the catalyst employed being a calcium salt of the unsubstituted halfester of succinic acid with diethylene glycol monoethyl ether, i.e. catalyst no. 2 from EP-A 0 337 239 cited at the outset.

The comparative examples are summarized in Table 3 below:

TABLE 3

| Comparative example | Catalyst quantity (% by wt.) | Initial alcohol | mol of EO/ mol of alcohol | Q index |
|---|---|---|---|---|
| 1 | 0.9 | n-$C_{12/14}$ | 4 | 1000 |
| 2 | 0.9 | n-$C_{12/14}$ | 6 | 1300 |

The alkoxyates of Comparative Examples 1 and 2 are highly cloudy.

We claim:

1. A process for the preparation of alkoxylates comprising alkoxylating a compound containing at least one active hydrogen atom in the presence of a catalyst wherein said catalyst contains at least one alkaline earth metal salt of an alkyl- or alkenylsuccinic monoester of the formulae (I) and (II) below

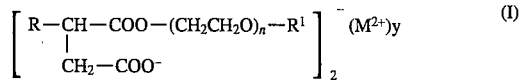

(I)

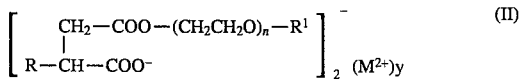

(II)

in which

R is $C_8$ to $C_{30}$ alkyl or $C_8$ to $C_{30}$ alkenyl, n is a number from 0 to 6, $R^1$ is $C_1$ to $C_{18}$ alkyl or $C_3$ to $C_{18}$ alkenyl or hydrogen, if n is 1 or >1, M is Ba, Ca or Sr, and Y is a number from 0.9 to 1.8.
and wherein from 10 to 70% of the titratable alkalinity of said alkaline earth metal salt of an alkyl- or alkenylsuccinic monoester of the formula (I) or (II) has been neutralized by an inorganic acid which forms salts of low solubility in water with the cations Ba, Ca or Sr.

2. A process for the preparation of alkoxylates comprising alkoxylating a compound containing at least one active hydrogen atom in the presence of a catalyst wherein said catalyst contains at least one alkaline earth metal salt of an alkyl- or alkenylsuccinic monoester of the formulae (I) and (II) below

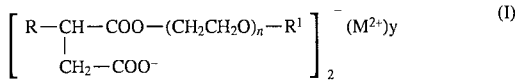  (I)

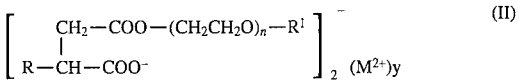  (II)

in which
R is $C_8$ to $C_{30}$ alkyl or $C_8$ to $C_{30}$ alkenyl,
n is a number from 0 to 6,
$R^1$ is $C_1$ to $C_{18}$ alkyl or $C_3$ to $C_{18}$ alkenyl or hydrogen, if n is 1 or >1,
M is Ba, Ca or Sr, and
y is a number from 0.9 to 1.8,
and wherein said catalyst is formed from an alkanol and a substituted succinic anhydride and converted into the Ba, Ca or Sr salt form in the same reaction zone in which the alkoxylating step is carried out.

3. The process as claimed in claim 2, wherein from 10 to 70% of the titratable alkalinity of said alkaline earth metal salt of an alkyl- or alkenylsuccinic monoester of the formula (I) or (II) is neutralized by an inorganic acid which forms salts of low solubility in water with the cations Ba, Ca or Sr.

4. The process as claimed in claim 1, wherein R is a $C_9$ to $C_{20}$ alkyl or a $C_9$ to $C_{20}$ alkenyl, n is a number from 0 to 3, $R^1$ is a $C_1$ to $C_{12}$ alkyl or a $C_3$ to $C_{12}$ alkenyl or hydrogen if n is 1 or >1, y is a number from 1 to 1.3, and M is Ca.

5. The process as claimed in claim 1, wherein R is a $C_9$–$C_{20}$ alkenyl and $R^1$ is a $C_1$ to $C_{12}$ alkyl.

6. The process as claimed in claim 1, wherein said alkaline earth metal salt of an alkyl- or alkenylsuccinic monoester of the formula (I) or (II) has been obtained by reacting an alkyl- or alkenylsuccinic monoester with an oxide, carbonate or hydroxide of barium, calcium or strontium in a quantity of from 0.9 to 1.8 mol per 2 mol of said alkyl- or alkenylsuccinic monoester.

7. The process as claimed in claim 1, wherein said inorganic acid is sulfurous acid, sulfuric acid, phosphorous acid or phosphoric acid.

8. The process as claimed in claim 1, wherein said catalyst is present in a quantity of from 0.1 to 5% by weight based on the quantity of said compound containing at least one active hydrogen atom.

9. The process as claimed in claim 1, wherein said catalyst is present in a quantity of from 0.5 to 3% by weight based on the quantity of said compound containing at least one active hydrogen atom.

10. The process as claimed in claim 1, wherein said compound containing at least one active hydrogen atom contains a hydroxyl group.

11. The process as claimed in claim 10, wherein said alkoxylating step is carried out by ethylene oxide, propylene oxide, or a mixture thereof.

12. The process as claimed in claim 1, wherein said compound containing at least one active hydrogen atom contains a fatty alcohol and said alkoxylating step is carried out by ethylene oxide, propylene oxide, or a mixture thereof.

13. The process as claimed in claim 1, wherein said alkoxylating step is carried out by an alkoxylating compound present in a quantity from 2 mole to 15 mol per mole of said compound containing at least one active hydrogen atom.

* * * * *